United States Patent [19]

Isaacson et al.

[11] Patent Number: 5,313,809

[45] Date of Patent: May 24, 1994

[54] INSULATING WRAP

[76] Inventors: Gary S. Isaacson, 56 Lincoln Rd., Sudbury, Mass. 01776; Lansing A. Old, 607 Lowell Rd., Concord, Mass. 01742

[21] Appl. No.: 85,685

[22] Filed: Jul. 2, 1993

Related U.S. Application Data

[63] Continuation of Ser. No. 837,393, Feb. 19, 1992.

[51] Int. Cl.$^5$ .............................. F25D 3/08; A61F 7/00
[52] U.S. Cl. ...................................... 62/530; 62/457.2; 62/457.4; 62/529; 156/145; 156/285; 607/114
[58] Field of Search ................. 62/457.4, 457.1–457.3, 62/459, 529, 530; 128/403; 156/145, 285

[56] References Cited

U.S. PATENT DOCUMENTS

| | | | |
|---|---|---|---|
| H759 | 4/1990 | Jones | 128/403 X |
| 2,152,019 | 3/1939 | Bates | 62/530 |
| 2,589,577 | 3/1952 | Rosenthal et al. | 128/403 X |
| 2,602,302 | 7/1952 | Poux | 62/530 |
| 3,802,220 | 4/1974 | Pompo | 62/530 |
| 3,885,403 | 5/1975 | Spencer . | |
| 3,921,961 | 11/1975 | Hapgood | 62/457.1 X |
| 4,183,226 | 1/1980 | Moore . | |
| 4,223,043 | 9/1980 | Johnson . | |
| 4,324,111 | 4/1982 | Edwards . | |
| 4,344,303 | 8/1982 | Kelly, Jr. | 62/457.4 X |
| 4,399,668 | 8/1983 | Williamson | 62/530 X |
| 4,457,142 | 7/1984 | Bucher . | |
| 4,516,409 | 5/1985 | Hobbs, Jr. et al. . | |
| 4,573,581 | 3/1986 | Galloway et al. . | |
| 4,592,358 | 6/1986 | Westplate | 62/530 X |
| 4,605,006 | 8/1986 | Jacques | 62/530 X |
| 4,681,648 | 7/1987 | Maeda | 156/285 X |
| 4,700,706 | 10/1987 | Münch | 62/530 X |
| 4,748,823 | 6/1988 | Asano et al. | 62/530 X |
| 4,753,241 | 6/1988 | Brannigan et al. | 62/530 X |
| 4,909,877 | 3/1990 | Nakanishi | 156/145 |
| 4,953,550 | 9/1990 | Dunshee | 62/530 X |
| 4,986,089 | 1/1991 | Raab . | |
| 5,027,801 | 7/1991 | Grim | 128/403 X |

FOREIGN PATENT DOCUMENTS

| | | | |
|---|---|---|---|
| 0039317 | 11/1981 | European Pat. Off. | 62/530 |
| 2297362 | 12/1990 | Japan | 128/403 |

Primary Examiner—Henry A. Bennett
Assistant Examiner—Christopher Kilner
Attorney, Agent, or Firm—David Fink

[57] ABSTRACT

The present invention relates to a method of producing an insulated wrap intended for wrapping any desired item in order to maintain a given temperature, either hot or cold, for the desired item. The method basically consists of providing a die having a plurality of cavities each of which has evacuation means associated therewith, placing a flexible thermoformable film over the die and evacuating the cavities thereby to thermoform the film and create multiple pouches in the film material. The pouches are then filled with a eutectic chemical compound consisting of potassium chloride solution, and then overlying the pouch-filled film with an insulated sealing film. The insulated sealing film consists of a polyethylene film co-extruded to a layer of closed cell polyolefin foam. The sealing film acts as a thermo barrier. The wrap is completed by providing fastening means at opposed ends of the wrap in order to permit the wrap to be fastened about any desired item for temperature maintenance purposes. The invention further consists of providing a product manufactured according to the subject method.

11 Claims, 1 Drawing Sheet

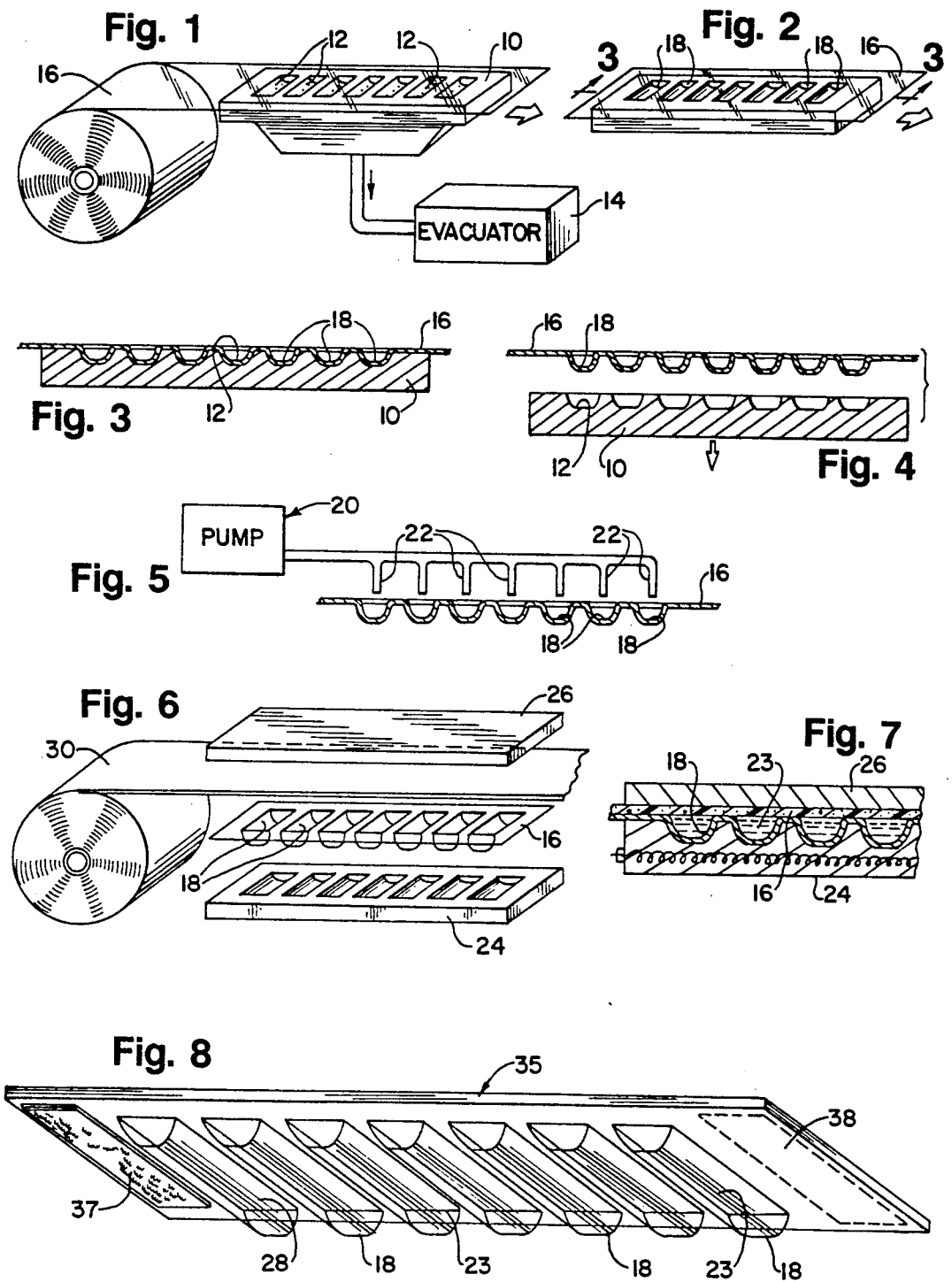

INSULATING WRAP

This is a continuation application of Ser. No. 07/837,393, filed Feb. 19, 1992.

BACKGROUND OF THE INVENTION

This invention relates to an insulated wrap, such as the type commonly used with beverage cans or other beverage containers, although useful to cool any desired item. The wrap of the present invention is constructed in a somewhat similar fashion to prior art type devices, however, the process whereby the wrap of the present invention is produced has been greatly improved to the extent that the entire process may be done by a single piece of machinery having multiple stages for performing each of the steps of the process. Furthermore, the wrap of the present invention is dramatically improved in terms of the construction of the wrap, as well as in terms of the eutectic solution utilized as a refrigerant.

Insofar as prior art type insulated wraps are concerned, various patents show alternate forms of existing type devices. For example, U.S. Pat. No. 4,986,089 shows a beverage wrap which is constructed in a linear fashion by producing a plurality of pouches along the length of the wrap. Each of the pouches self-contains a refrigerant therein, and in its completed format, is intended to wrap around a beverage can as illustrated in the drawings therein. It will be noted, however, that once constructed, the pouches are circular and/or elliptic in configuration, and hence, only the tangential portion of the pouch adjacent to the can will have any cooling impact upon the beverage can. Furthermore, the wrap as illustrated therein requires multiple steps and/or processes in order to construct the wrap, thereby making the wrap somewhat expensive to produce.

Still another patent illustrating an alternate form of a beverage wrap is shown in U.S. Pat. No. 4,831,842. As illustrated therein, the wrap consists of a multi-layered structure including an outer sheet formed from a nylon fabric having a rubber backing. There is also included an inner liner element which is sewn or otherwise secured to the inside wall of the outer sheet. The liner contains one or more liquid tight receptacles which are positioned between two sheets of thin polyester cotton thereby to create the liner. The inner liner element is then secured to the outer sheet as illustrated, by sewing or other fastening means. It will become evident that in order to create a wrap of this type, there are several individualized steps in the process which must be effected in order to create the outer sheet formed into a tubular member with the inner liner element secured thereto. Furthermore, from the above description, it is obvious that the receptacles containing the refrigerant must similarly be secured between two sheets of polyester cotton in order to create the inner liner element. Hence, the cost of production of such a wrap is prohibitively high, and it will also be appreciated that because of the manner in which the receptacles are formed, that only the part of the receptacle adjacent to the can will have the refrigerating effect. Furthermore, since the refrigerant receptacles are contained between two sheets of polyester cotton, the refrigerant compacity of the device is somewhat reduced.

U.S. Pat. No. 4,399,668 illustrates still another format for a beverage wrap which includes an inner coolant layer for wrapping about the container, which again contains multiple receptacles or cavities in which a coolant is contained, with the coolant layer being externally surrounded by an insulative layer. It is obvious from the description and the claims that the two layers are separately formed, and it must be mechanically manipulated in order to effectively place the wrap around a beverage container. It will also be appreciated that the coolant which is employed is one of the types generally sold under the Trademark, BLUE ICE, which is basically a gel type substance. Indeed, it is prevalent in the prior art that coolant or refrigerant which is utilized is a gel type solution which is intended to be placed in a freezer and frozen, and has characteristics of taking a period of time to defrost during which time it functions as a heat sink to cool the beverage about which it is wrapped.

Once again, it is evident from the review of the patent that multiple steps must be employed in order to create the wrap, and indeed, the inner coolant layer is separately formed from the outer insulating sheet, such that separate manufacturing processes must be employed.

A further type of beverage wrap is illustrated in U.S. Pat. No. 4,324,111. The wrap employed in the subject patent is created with multiple cavities in which a freezing gel solution is contained. As indicated previously, it is intended that the wrap be placed in a freezing compartment of some type, so that the gel will fully freeze. As shown in the drawings, once wrapped about the beverage container, the tangential sides of the circular pouches are positioned against the beverage container and function to perform the cooling process. It will be appreciated, however, that because only a part of the circular structure of each cavity is in tangential alignment with the beverage can, the cooling proficiency of the wrap is diminished.

U.S. Pat. No. 4,183,226 illustrates still another type of prior art beverage wrap which again is shown to be formed by a plurality of pouches in which a refrigerant of some type is employed. Once again, as with other prior art type wraps, it is apparent from review of the structure as indicated in the patent that the process for making such a wrap requires multiple processes in order to complete the construction of the wrap. As with other prior art devices, the cost of producing such products is reasonably high, and therefore, such types of wraps have not achieved any great degree of commercial success.

OBJECTS AND ADVANTAGES

The primary object of the present invention is to provide a process for creating an insulated wrap which permits the process to be performed by a single piece of machinery having multiple stages so that an insulated wrap may be created and produced through a single series of processes and in one process.

A further object of the present invention is to provide a process for constructing an insulated wrap which has multiple uses in terms of either cooling or heating characteristics for a wide variety of items, and not just limited to beverage cans or containers.

A further object of the present invention is to provide a low cost but highly efficient process for producing an insulated wrap which will expose to the item to be cooled or heated, a maximum amount of coolant surface area in order to achieve an even higher degree of heat exchange as between the item to be cooled and the refrigerant.

In conjunction with the foregoing objects, a further object of the present invention is to provide an insulated wrap wherein the refrigerant is formed from a potassium chloride solution which is utilized as the eutectic solution so that the subject eutectic solution provides a constant temperature while the compound is melting.

A further object of the present invention is to provide a method for forming an insulated wrap which includes the steps of providing a die having a plurality of cavities with each of the cavities having evacuation means associated therewith, placing a flexible thermoformable film over the die and overlying the plurality of cavities and evacuating the cavities to thermoform the film and create a film having multiple pouches formed therein. The process then includes the step of filling the pouches with a eutectic chemical compound solution which is designed to maintain and stabilize temperature, and overlying the pouch filled film with an insulated sealing film. The overlying film and the underlying film are sealed together by providing a heated sealing die from below the film and simultaneously providing a pressure plate above the film such that the top insulated sealing film is sealed to the underlying thermoformed and filled film by means of heat from below and pressure from above thereby to encapsulate the eutectic chemical compounds within the pouches to create the insulated wrap. Additionally, the method provides a final step for providing fastening means on the insulated wrap so that the wrap may be fastened about the desired item in order to achieve temperature maintenance.

A further object of the present invention is to provide an insulated wrap as a product made in accordance with the steps of the process identified above.

SUMMARY OF THE INVENTION

In summary, the present invention provides a method for producing an insulated wrap of the type which may be utilized to wrap around any desired item to maintain a given temperature. Principally, the wrap is designed to be a coolant or refrigerant for a given product or item, although it is contemplated to be within the scope of the present invention to create a wrap in accordance with the steps of the process of the present invention which may be used as a heating device.

The purpose of the present invention is to provide an improved process for manufacturing and producing an insulated wrap such that a single piece of machinery is designed to perform multiple functions in series and avoid the necessity of complex and multiple process steps incident to creating an insulated wrap. In addition, the present invention provides a eutectic chemical solution which consists of a solution of potassium chloride in water which has temperature maintenance properties far superior to any existing refrigerant or coolants used in insulated wraps.

In summary, the method of the present invention includes the steps of providing a die having a plurality of cavities each of which has evacuation means associated therewith, placing a flexible thermoformable film over the die and overlying the plurality of cavities, and evacuating the cavities thereby to thermoform the film and create a film having multiple pouches formed therein. Once, the pouches have been created, the product is advanced to a filling station where the pouches are filled with a eutectic chemical compound solution which is designed to maintain and stabilize temperature, and then overlying the pouch-filled film with an insulated sealing film. The process is completed by providing a heated sealing die from below the film and simultaneously providing a pressure plate above the film whereby the top insulated sealing film is sealed to the underlying thermoformed and filled film by means of heat from below and pressure from above thereby to encapsulate the eutectic chemical compound contained within the pouches and creating an insulated wrap. Finally, the product is advanced to a final station where fastening means are secured to the wrap such that the wrap may be fastened about the desired item in order to achieve temperature maintenance.

Hence, the present invention provides a novel manufacturing process especially in connection with the provision of a heated sealing die which is positioned below the composite film, and a pressure plate which is positioned above the film, so that heat is provided for laminating the films together from below while pressure is applied from the top. It is known that heating the polyolefin foam to or above 180° F. will destroy the foam cell structure, and the material will break down and lose its insulating properties. The present process will not destroy the insulator barrier which is formed as a part of the overlying sealing film. In addition, the present invention provides a new form of coolant or refrigerant consisting of a solution which is a mixture of nineteen point seventy-five (19.75%) percent by weight potassium chloride dissolved in eighty point twenty-five (80.25%) percent by weight water. This particular mixture, it is found, will freeze at 11° F. and will provide and maintain a constant temperature while the compound is melting. In that manner, one maintains a low temperature for an extended period of time, and further, remains at its 11° F. temperature until it is completely melted. This occurs primarily because the eutectic solution goes through a change of state, i.e. from solid to liquid, which results in the temperature maintenance characteristic as defined.

Finally, the present invention provides an insulated wrap made in accordance with the process of the present invention which has improved properties and characteristics in terms of its ability to maintain temperature over a longer period of time.

BRIEF DESCRIPTION OF DRAWINGS

With respect to the drawings, the drawings illustrate the process of the present invention, as well as the product formed thereby.

FIG. 1 is a perspective view of the initial step of the method wherein a thermoformable film is positioned over a die having a plurality of cavities;

FIG. 2 illustrates the thermoformable film being formed in the dies as the evacuator evacuates air from the die cavities;

FIG. 3 is a side elevational view in cross section, taken in the direction of the arrows along the line 3—3 of FIG. 2 and shows the thermoformable film as formed in the die;

FIG. 4 illustrates the next step of the method with the thermoformable film being removed from the die in preparation for filling;

FIG. 5 shows the thermoformable film positioned under the filling nozzle for filling the pouches with the eutectic chemical solution.

FIG. 6 shows the next step of the method with the sealing film being positioned over the thermoformed and filled film in preparation for the final encapsulating step;

FIG. 7 is a side elevational view, in cross section, showing the heated die from below and the pressure plate from above incident to the sealing process for completing the manufacture of the insulated wrap; and FIG. 8 is a perspective view showing an insulated wrap product manufactured in accordance with the method illustrated in FIGS. 1 through 7.

DETAILED DESCRIPTION OF DRAWINGS

With respect to the drawings, FIGS. 1 through 7 illustrate the method of the present invention. As previously indicated, the present invention is intended to permit the production of an insulated wrap on a single piece of machinery having multiple stations such that segregated manufacturing processes are not required. An insulated wrap may be completely created and produced by a single piece of equipment having multiple stations so that the steps of the process are completed in sequence, and a fully formed insulated wrap is created. This eliminates the necessity of separate sewing or stiching processes, taken in combination with separate laminating steps and filling steps.

FIG. 1 illustrates the first step of the process by showing the provision of a die 10 which contains a series of cavities 12 arranged in linear fashion. The lower end of the die 10 is connected to an evacuator 14 which functions to evacuate the air from each of the cavities 12. It will be appreciated that each of the cavities 12 has appropriate apertures at the lower end of each cavity 12 which are connected to a manifold system and to the evacuator 14 such that once the evacuator is activated, each of the cavities 12 may have the air evacuated therefrom.

A roll of thermoformable film 16 is provided, and at the inception of the process, the leading edge of the roll of film 16 is moved into position over the die 10 and positioned in overlying relationship with respect to the cavities 12. The evacuator 14 is then activated, and air is then removed from each of the cavities 12 such that the film 16 is thermoformed by being drawn into the cavities 12.

As shown in FIG. 2, as the film 16 is drawn into the cavities 12, a series of pouches 18 are created as more particularly illustrated in FIG. 3. FIG. 4 illustrates the film 16 having the pouches 18 formed therein which will be held in position by the machinery (not shown) as the die 10 is moved downwardly and out of contact with the formed film 16.

FIG. 5 illustrates the next sequential station in that the thermoformed film 16 is moved to a pumping station 20 which has a series of nozzles 22 which are positioned immediately above respective pouches 18. When the pump 20 is activated, the eutectic solution will be pumped on a volume basis thereby to fill the pouches 18 with the eutectic chemical solution. The film is then moved to the final station as illustrated in FIG. 6, which provides a heated die 24 positioned below the thermoformed and filled film, and a pressure plate 26 positioned above the film. A roll stock of sealant film 30 is provided which is moved into position over the formed film 16 which is formed with the pouches 18 and which are now filled with the eutectic solution. As illustrated in FIG. 7, the lower heated die 24 is moved upwardly into position under the film 16 while simultaneously, the pressure plate 26 is moved downwardly into position above the sealant film as illustrated therein. As further shown in FIG. 7, the eutectic solution 23 is in place in each of the pouches 18 such that when the sealant film is positioned above the film 16, and the sealing process occurs, the eutectic solution 23 will be encapsulated within the pouch 18.

As shown in FIG. 8 of the drawings, once the lower heated die 24 and upper pressure plate 26 are moved out of position, the insulated wrap is fully formed although as a final step of the process, appropriate fastening means may be provided at both ends of the insulated wrap. As shown in FIG. 8, the final insulated wrap 35 is shown to be fully formed and includes fastening means consisting of the male VELCRO (Trademark) brand hook and loop fastener 37 and corresponding female VELCRO (Trademark) brand hook and loop fastener 38 secured to the wrap 35. The wrap as formed now includes the pouches 18 which, in cross-section, are in the form of a substantially trapezoidal configuration and are fully filled with the eutectic solution 23.

As previously indicated, most all of the prior art and existing wraps which are intended to either refrigerate or heat a desired item are either expensive, or too expensive to produce, or are non-performing for substantial periods of time. Furthermore, from a manufacturing standpoint, the existing prior art devices require multiple step operations with different types of machinery, and often, a great degree of hand labor.

Insofar as the refrigerant is concerned, most of the beverage container wraps are fairly rigid in design and therefore cause a freezer space problem when the user attempts to freeze the wrap for cooling purposes. For example, most of the medical related wraps require a gelatinous (non-freezing) refrigerant to allow easy skin contact. The present wrap, while articulated, will still easily freeze to a solid. Due to the pouch configuration, this will allow maximum skin contact. It will therefore be appreciated that the wrap of the present invention may also be used for medical purposes in addition to being used as an insulated wrap for beverage cans.

The present invention eliminates virtually all of the problems noted above. For example, the refrigerant in the present invention will freeze at 11° F., and has the capacity to not only reduce the temperature of the item for which it is to be used as a refrigerant, but will maintain the temperature of the frozen object in a frozen state. The eutectic solution of the present invention is designed such that it will maintain its temperature while melting, and hold that temperature until it is completely melted. Hence, by using the proper compounds and the appropriate amount of compounds, coupled with an adequate amount of insulation, the present invention achieves a wide range of usage with respect to temperature sensitive products. Hence, as a cooling device, the eutectic composition of the present invention when chilled or frozen, becomes a heat sink, and as a heating device, provides specific heating needs required by given food products or packages.

Furthermore, the present invention, while as illustrated in the drawings and shown to be rectangular in shape with multiple pouches arranged in a linear alignment, may be made to any desired shape with any number of pouches depending upon the specific need or market for which the product wrap is designed. The wrap of the present invention, for example, has application to medical usage as well as a beverage container wrap. It will be appreciated that the method as described above would be altered only insofar as a particular die would have to be cut and provided for the machine in order to permit the thermoformable film to be thermoformed into the desired shape with a desired number of pouches. Other than the shape of the die, the process may be utilized for creating an insulated wrap in accordance with the present invention. In this connection, it will be appreciated that the size and shape of the cavity is designed to allow for specific amounts of the eutectic composition that would be necessary to achieve the desired performance. For example, it might be necessary to have the cavity deep enough to accept eight (8 oz.) ounces of the eutectic solution in order to chill a wine bottle, but for chilling a twelve (12 oz.) ounce beverage can, it might only be necessary to have the cavity accept four (4 oz.) ounces of the eutectic solution. The process of the present invention including the machinery employed permits, hence, a wide range of insulated wraps to be created.

Insofar as the shape of the pouches is concerned, it will be observed that the pouches of the present invention are designed to be substantially trapezoidal in configuration. It will be recollected that most of the prior art wraps create pouches which are circular or elliptical in configuration. When so constructed, each pouch will only touch the item to be cooled along a tangential line, and hence, a great deal of the cooling effect of the refrigerant in the pouch is lost. The pouches of the present invention are shown to be tapered along the side walls culminating in a substantially flat bottom. Hence, the amount of surface area of the contained coolant which touches the item to be cooled is substantially increased, thereby greatly enhancing the cooling properties of the insulated wrap of the present invention.

Another distinguishing feature of the present invention is the method of sealing the sealant film onto the thermoformed film. As previously indicated, the sealing film is actually composed of a sealing film co-extruded with an insulator. The sealing film is actually a layer of 1/16 inch polyolefin foam co-extruded to 3 mils of linear low density polyethylene, which functions as the insulating barrier. In view of the use of the closed cell polyolefin foam, it was necessary to design the process so that incident to the sealing process of sealing the sealant film to the thermoformed film, the use of heat would not destroy the insulator. For this reason, the present process is designed to apply a heated die from below the thermoformed film, while simultaneously applying a pressure plate from above and by applying the appropriate pressure and the correct amount of heat, the sealant film may be successfully laminated to the thermoformed film without any destruction of the wrapped material, and especially the insulator material.

As previously indicated, the present process is designed to operate within the framework of a single machine having multiple stations so that the product which is produced is a completed insulated wrap and eliminates the need for any extraneous steps or hand labor. Furthermore, the insulated wrap of the present invention employs the use of eutectic solution consisting of potassium chloride which is a mixture of nineteen point seventy-five (19.75%) percent by weight potassium chloride dissolved in eighty point twenty-five (80.25%) percent by weight water. This type of refrigerant has not heretofore been utilized in insulated wraps, and indeed, as indicated previously, most of the insulated wraps or coolant structures employ a gelatinous, non-freezing substance, as the refrigerant. The use of the eutectic solution such as potassium chloride therefore permits the ability to maintain a low temperature for an extended amount of time, and further, will remain at its frozen temperature until it is completely melted. Furthermore, the use of this solution is compatible with home use since most home freezers do not have the capability to freeze a refrigerant at extremely low temperatures. Hence, this solution when employed in a beverage wrap for home use may be easily frozen in a standard home freezer. Furthermore, a potassium chloride solution is non-toxic and therefore safe in a home use environment.

Another feature of the present invention relates to the design of the pouches which are formed on the insulated wrap. The typical prior art devices as indicated previously also employ pouches, but the pouches are on both sides, or that is, circular or substantially circular in configuration thus creating an arc that greatly reduces the surface contact of the pouch with the product. It is deemed desirable to create a pouch where more surface area of the compound is permitted to be in touching contact with the temperature sensitive products so that the wrap will perform more effectively.

For example, in U.S. Pat. No. 4,324,111 the pouches shown therein have a smaller degree of surface area in contact with the item to be cooled as compared to the pouches formed in the wrap of the present invention. For this reason, and as previously indicated, the present insulated wrap can achieve a more consistant and greater degree of heat exchange capability.

In accordance with the present invention, by thermoforming the film into the desired shape, one can achieve maximum surface contact for product performance. It will therefore be appreciated from the above description that the present invention provides an improved insulated wrap product, and furthermore, provides an improved process for creating such a product. The process of the present invention permits the product to be produced on an economically feasible basis, and furthermore, improves the performance and temperature maintenance ability of the insulated wrap product itself in connection with any desired product usage.

While there has been described what is at present considered to be the preferred embodiment of the invention, it will be understood that various modifications may be made therein all of which are considered within the true spirit and scope of the present invention.

We claim:

1. A method of forming an insulated wrap comprising the steps of:
   providing a die having a plurality of cavities, each of said cavities having evacuation means associated therewith,
   said cavities being provided in a linearly aligned disposition;
   placing a flexible thermoformable film over said die and overlying said plurality of cavities, said thermoformable film being formed by a film layer of 1 mil of thermoforming nylon coextruded to 3 mils of linear low density polyethylene,
   evacuating said cavities thereby to thermoform said film and create a film having multiple pouches formed therein,
   filling said pouches with a eutectic chemical compound which is designed to maintain and stabilize temperature, said eutectic chemical compound consisting of a solution of potassium chloride,
   overlying said pouch-filled film with an insulating sealing film,
   said insulating sealing film consisting of a layer of 1/16 inch of polyolefin foam co-extruded to 3 mils of linear low density polyethylene, providing a heat sealing die from below the film and simultaneously providing a pressure plate from above the film whereby the top insulated sealing film is sealed to the underlying thermoformed and filled film by means of heat from below and pressure from above thereby to encapsulate the eutectic chemical compound consisting of potassium chloride contained within the pouches and creating an insulating wrap, and providing fastening means on said insulated wrap such that said wrap may be fastened about the desired item to achieve temperature maintenance.

2. The method of claim 1 wherein said solution of potassium chloride consists of a nineteen point seventy-five (19.75%) percent by weight solution of potassium chloride in eighty point twenty-five (80.25%) percent by weight water.

3. The insulated wrap product made in accordance with the method of claim 1 above.

4. The insulated wrap product made in accordance with the method of claim 1 above.

5. A method of forming an insulating wrap, comprising the steps of:

providing a die having a plurality of cavities defined therein, and evacuating means associated with each cavity and operable for producing a low pressure in each cavity;

positioning a first film over said cavities; said first film being a flexible thermoformable film;

creating a low pressure in each cavity to deform said first film to define the shape of said cavity;

filling the first film cavities with a liquid capable of being frozen;

covering said first film with a second film; said second film having a layer facing said first film which is heat sealable layer and a layer facing away from said first film which is relatively thermally insulating layer; and heating sealing said first and said second films together to encapsulate said liquid by applying heat to said first film below said second film and pressure to said second film above said first film;

whereby, said first and second film form an insulating wrap having a plurality of pouches of liquid with substantially no damage to said insulating layer.

6. The insulating wrap as claimed in claim 5, wherein said thermally insulating layer comprises a material seriously degraded by elevated temperatures and said heating sealing step is carried out to avoid degrading said insulating material.

7. The insulating wrap as claimed in claim 6, wherein said insulating layer comprises a polyolefin foam.

8. The insulating wrap as claimed in claim 5, further comprising means for attaching said wrap to an object.

9. The insulating wrap as claimed in claim 8, wherein said attaching means comprises a pair of interlocking hook and loop portions.

10. The insulating wrap as claimed in claim 5, wherein said liquid is an eutectic solution.

11. An insulating wrap made with the method comprising the steps of:

providing a die having a plurality of cavities therein, and evacuating means associated with each cavity and operable for producing a low pressure in each cavity;

positioning a first film over said cavities; said first film being a flexible thermoformable film;

creating a low pressure in each cavity to deform said first film to define the shape of said cavity;

filling the first film cavities with a liquid capable of being frozen;

covering said first film with a second film; said second film having a layer facing said first film which is heat sealable layer and a layer facing away from said first film which is relatively thermally insulating layer; and heating sealing said first and said second films together to encapulate said liquid by applying heat to said first film below said second film and pressure to said second film above said first film;

whereby, said first and second film form an insulating wrap having a plurality of pouches of liquid with substantially no damage to said insulating layer.

* * * * *